United States Patent [19]

Schlosser

[11] Patent Number: 5,052,588

[45] Date of Patent: Oct. 1, 1991

[54] AMPULE HAVING A FRACTURING OUTLET END, A SWELLABLE PISTON AND A BREAKABLE END FOR GAINING ACCESS TO THE PISTON

[75] Inventor: Mark S. Schlosser, Seattle, Wash.

[73] Assignee: SpaceLabs, Inc., Redmond, Wash.

[21] Appl. No.: 528,684

[22] Filed: May 24, 1990

[51] Int. Cl.⁵ .......................... B65D 47/10; B67D 5/00
[52] U.S. Cl. ...................................... 222/80; 222/386;
  222/541; 222/1
[58] Field of Search ................... 222/1, 386, 386.5, 81,
  222/80, 541, 326, 327; 92/172; 220/93

[56] References Cited

U.S. PATENT DOCUMENTS

| | | | |
|---|---|---|---|
| 2,742,902 | 4/1956 | Scheibler | 222/386 X |
| 2,887,253 | 5/1959 | Biedenstein | 222/327 |
| 2,941,699 | 6/1960 | Schmidt et al. | 222/327 |
| 3,667,657 | 6/1972 | Chiquiar-Arias | 222/541 |
| 4,331,267 | 5/1982 | Duncan et al. | 222/327 X |
| 4,350,271 | 9/1982 | Eckenhoff | 222/386.5 |

Primary Examiner—Kevin P. Shaver
Attorney, Agent, or Firm—Seed and Berry

[57] ABSTRACT

A positive displacement ampule for storing a fluid therein and dispensing the fluid therefrom. The ampule includes an elongate vessel for storing the fluid having a large diameter base portion at one end thereof joined to a small diameter stem portion at the other end thereof, a piston disposed in the vessel at the base end thereof for forcing the fluid from the vessel and a push rod for fracturing the base end of the vessel and pushing the piston so as to pump the fluid from the vessel after the stem thereof has been fractured. The stem and the base of the vessel have weakened areas which permit the fracturing thereof. The positive displacement ampule is manufactured by providing the elongate vessel with the stem end of the vessel being open and the base end of the vessel being closed, injecting a monomer liquid into the vessel through the open stem end thereof, polymerizing the liquid so as to convert the liquid to a solid designed to function as a piston, injecting the fluid into the vessel through the open stem end thereof in such a manner so as to maintain the fluid between the piston and the stem end and sealing the stem end of the vessel.

11 Claims, 3 Drawing Sheets

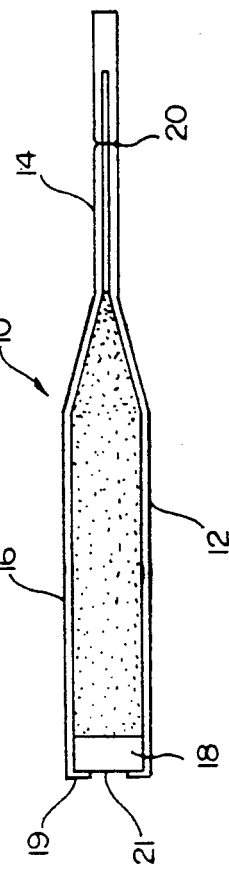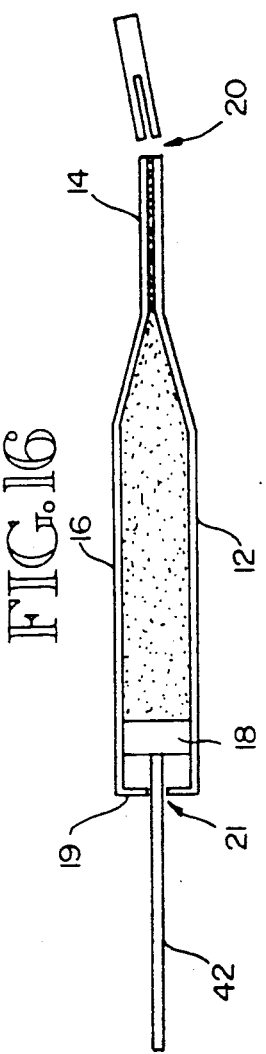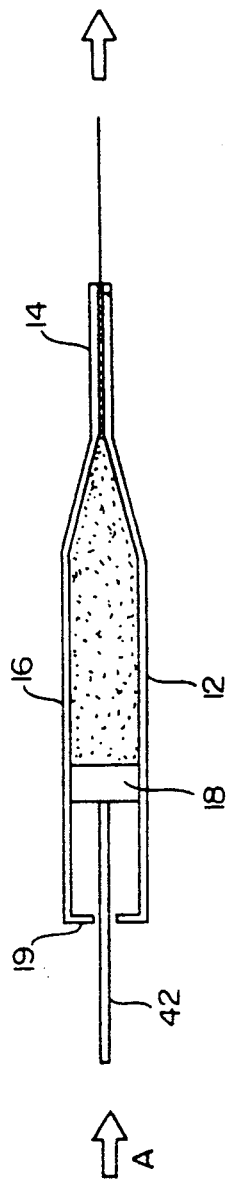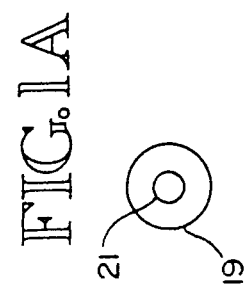

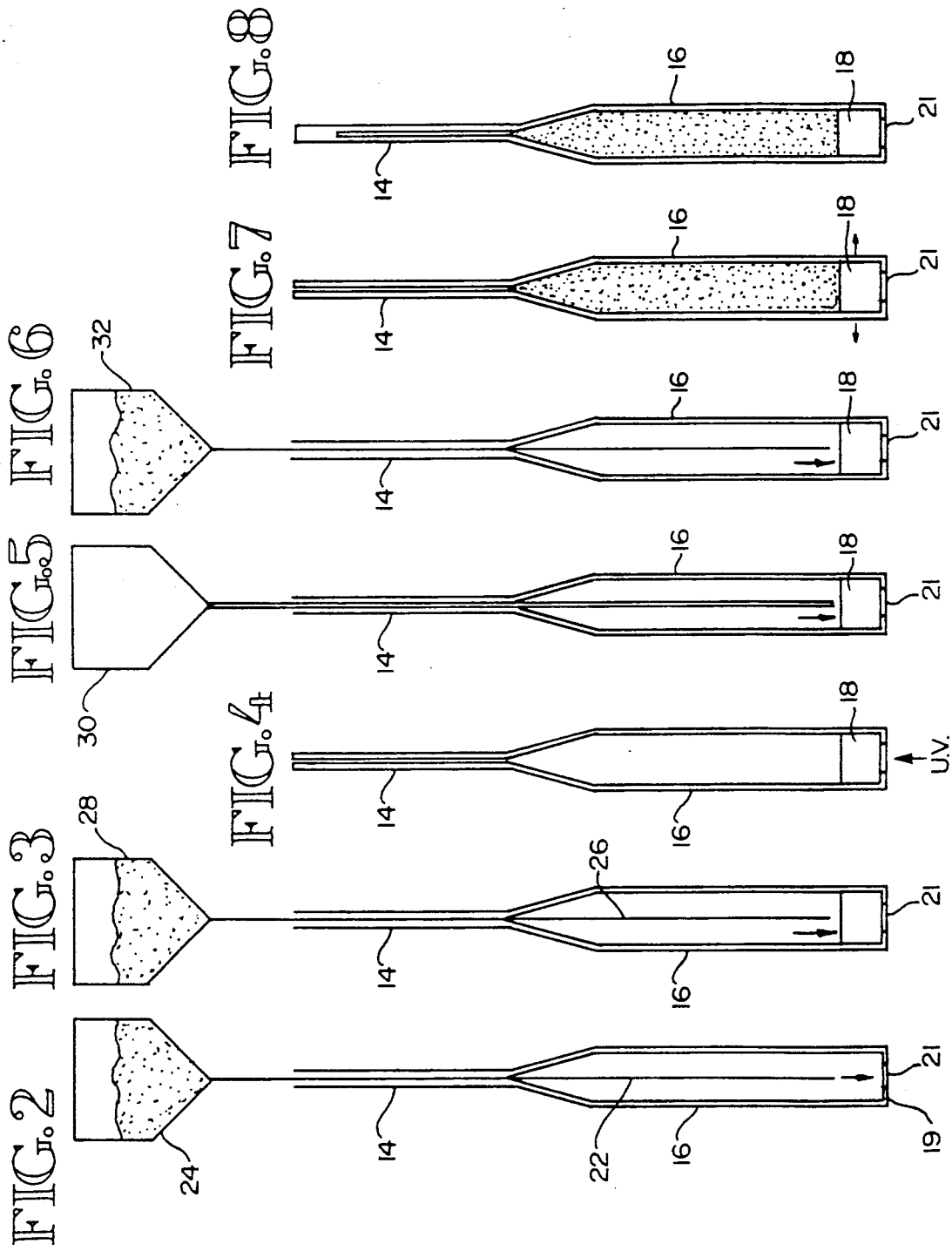

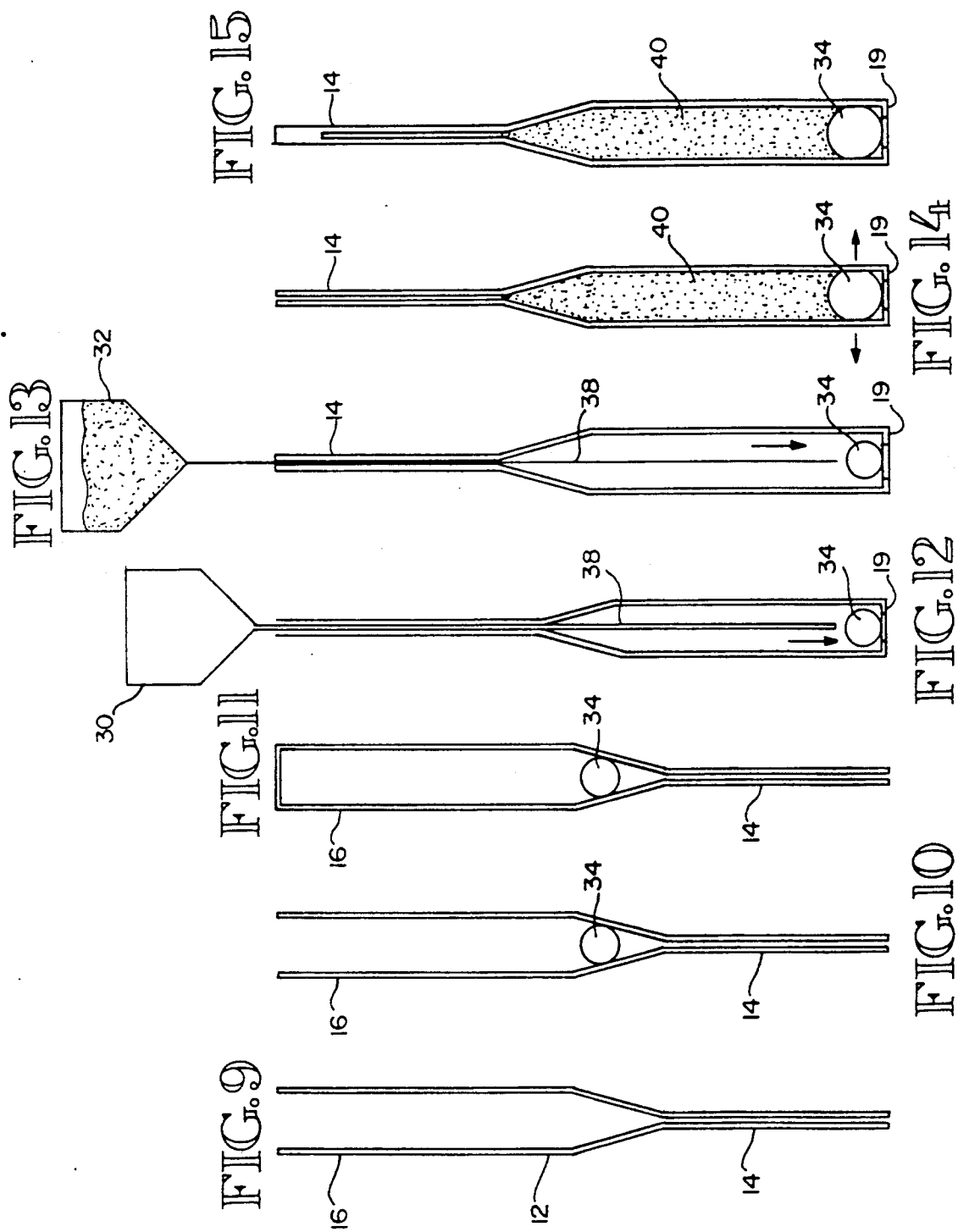

AMPULE HAVING A FRACTURING OUTLET END, A SWELLABLE PISTON AND A BREAKABLE END FOR GAINING ACCESS TO THE PISTON

TECHNICAL FIELD

This invention relates to a storage device, and more particularly, to a storage device having a positive displacement dispenser for dispensing fluid therefrom.

BACKGROUND OF THE INVENTION

There are three types of ampules that are presently known: a pressurized ampule, an evacuated ampule and non-pressurized ampule. The pressurized ampule contains fluid or powder which is at a pressure greater than atmospheric pressure such that the fluid or powder is propelled from the ampule by breaking the tip of the ampule. This type of ampule is manufactured by introducing the fluid or powder into the opened tip end of the ampule in a pressurized atmosphere and thereafter sealing the ampule.

The evacuated ampule is primarily designed for conducting chemical analyses of water. The evacuated ampule contains a fluid at a pressure that is less than atmospheric pressure. The analysis is conducted by breaking the tip of the ampule while dispersed in the water being analyzed. Due to the low pressure in the ampule relative to the environment, the water is drawn into the ampule and mixes with the analyzing fluid or powder. The water is analyzed by observing the change in color of the mixed fluid.

The non-pressurized ampule includes stem portions at opposite ends and is filled with a fluid, such as a medicine, at atmospheric pressure. To dispense the fluid, both stems are broken and the fluid is drained from the ampule.

There are no known ampules having positive displacement capabilities which permit the user to pump the fluid contained in the ampule therefrom. Further, there are no known positive displacement devices which store fluids with gases trapped in predictable volume regions.

SUMMARY OF THE INVENTION

The present invention resides in a positive displacement ampule which allows the user to pump the fluid therefrom. The positive displacement ampule comprises an elongate vessel for storing a fluid therein having a large diameter base portion at one end thereof joined to a small diameter stem portion at the other end thereof, a piston disposed in the vessel at the base end thereof for forcing the fluid from the vessel and a push rod for fracturing the base end of the vessel and pushing the piston so as to pump the fluid from the vessel after the stem thereof has been fractured. The stem and the base of the vessel have weakened areas which permit the fracturing thereof by conventional means.

The positive displacement ampule is manufactured by manufacturing the elongate vessel with the stem end of the vessel being open and the base end of the vessel being closed, injecting a monomer liquid into the vessel through the open stem end thereof, polymerizing the liquid so as to convert the liquid to a solid, the solid being designed to function as a piston, injecting the fluid into the vessel through the open stem end thereof in such a manner as to maintain the fluid between the piston and the stem and sealing the stem end of the vessel.

According to an alternative embodiment, both the stem end and the base end of the vessel are initially open and a solid polymer is placed in the large diameter portion of the vessel. Thereafter, the base end is sealed and the fluid is injected through the open stem end which is then sealed. The fluid causes the polymer to expand against the interior wall of the vessel so as to act as a piston.

BRIEF DESCRIPTION OF THE DRAWINGS

FIG. 1 is an elevational view of the positive displacement ampule according to the present invention;

FIG. 1a is an end view of the positive displacement ampule of the FIG. 1 embodiment;

FIGS. 2-8 are elevational views illustrating a method of manufacturing the positive displacement ampule according to the primary embodiment of the invention;

FIGS. 9-15 are elevational views illustrating an alternate method of manufacturing the positive displacement ampule according to a second embodiment of the invention; and FIGS. 16 and 17 are elevational views illustrating a method by which the fluid in the positive displacement ampule is pumped therefrom.

DETAILED DESCRIPTION OF THE INVENTION

Referring to FIGS. 1 and 1a, the positive displacement ampule 10 is an elongate vessel 12 having a smaller diameter stem 14 at one end thereof joined to a relatively large diameter portion 16 at the other end thereof. A cylindrical piston 18 is disposed at the base 19 of the large diameter portion with fluid being contained above the piston extending up to the bottom of the stem.

Provided in the stem 14 is an annular ceramic band 20 designed to permit the user to break the stem at a predetermined location so as to allow the fluid to exit. Correspondingly, the base 19 has a weakened area 21 at the central portion thereof such that the user can fracture that portion of the base with a firing pin-like device in order to push the piston 18 and force the fluid from the vessel through the fractured stem. The weakened area 21 can be formed by, for instance, reducing the thickness of the base of the vessel or scoring a circle in the base.

The vessel is capable of being filled to greater than 90% of its volume. Moreover, the stem design insures that all of the gases in the vessel are trapped in the stem 14 of the vessel. Maintaining the position of the gas bubble at the leading edge of the flow is important in providing a negative fluid meniscus the leading edge of which serves to scrape previous fluids from the walls of the path, such as in a flow cell, so as to prevent the previous fluids from mixing with the present fluid thereby preventing what is commonly referred to as "carry-over". This is accomplished by maintaining the inside diameter of the stem less than 1 mm such that the stem acts as a capillary tube. In this manner, the surface tension of the fluid acts to prevent the fluid from mixing with the gases, thereby maintaining the gases in the stem.

The vessel can be made out of a gas impermeable material such as glass so as to insure that the glass in the fluid do not permeate the vessel. Alternatively, the vessel can be made out of gas permeable material such as plastic if maintaining the gas concentration in the fluid is not important.

Two alternative methods of manufacturing the ampule are illustrated in FIGS. 2 through 8 and FIGS. 9 through 15, respectively. Referring to FIG. 2, initially, the vessel 12 is open at the top of the stem 14 and closed at the base 19 of the large diameter portion 16. A needle 22 is inserted into the opening and a coating agent 24 applied to the interior of the base. The coating agent is designed to insure that the piston liquid that is subsequently injected and polymerized does not stick to the interior of the vessel 12. After coating the base, another needle 26 is inserted through the opening and a monomer 28 containing a polymerizing agent in the form of a liquid is injected into the vessel as shown in FIG. 3. An important characteristic of the polymerizeable monomer is that, once polymerized, it expands when exposed to an aqueous solution (i.e., it is water-swellable). The specific monomer utilized is in the HEMA family and has the chemical name POLY-HYDROXYETHYL-METHACRYLATE. An example of a polymerizing agent is BENZYL PEROXIDE (which is polymerized by heat) or 2,2,DIETHOXY ACETALPHENONE (which is polymerized by ultraviolet light).

As illustrated in FIG. 4, the monomer liquid is polymerized by exposing the liquid to ultraviolet light or, alternatively, to heat. By polymerizing the liquid, a cylindrical piston is formed which, as described above, is utilized to force the fluid in the vessel therefrom.

If it is important to maintain the gas concentration of the fluid in the vessel, as illustrated in FIG. 5, after the fluid has been polymerized, the vessel 12 may be filled with a tonometered gas mixture 30 and, thereafter, a tonometered calibrant fluid 32, as illustrated in FIG. 6. The calibrant fluid contains a known amount of carbon dioxide, oxygen and nitrogen in terms of partial pressure. This is important because when analyzing the oxygen and carbon dioxide content of blood the flow cell must be calibrated by passing a calibrant fluid having a known amount of carbon dioxide and oxygen into a flow cell. In order to prevent the calibrant fluid from releasing any of its gases and to thereby maintain the proper ratio of gases in the calibrant fluid when injecting the fluid into the vessel, it is recommended that the vessel be filled with a gas mixture having the same percentage of gases as the calibrant fluid. Accordingly, as noted above, a gas mixture 30 having a known percentage of gases, which are correspondingly present in the calibrant fluid 32, is injected into the vessel prior to the injection of the calibrant fluid.

Subsequent thereto, as noted above, the tonometered fluid 32 is injected utilizing a needle, as illustrated in FIG. 6 such that the fluid extends up to or beyond the bottom of the stem 14. At this time, the piston 18 swells sufficiently to press firmly against the interior wall of the vessel to thereby provide an adequate piston seal, as shown in FIG. 7. Specifically, the piston seals the fluid 32 in the vessel 12 such that when the weakened central area 21 of the base 19 is fractured the fluid does not leak past the piston and from the vessel. After the fluid has been injected into the vessel, the top of the stem is sealed, as shown in FIG. 8.

While the above description describes the manner in which a monomer liquid is injected into the vessel and thereafter polymerized to form the piston, it is of course understood that the invention is not intended to be limited to this embodiment. Rather, any liquid (i.e., any viscous substance) that can be converted to a solid may be used to form the piston. For instance, an epoxy liquid could be injected into the vessel and thereafter converted to a solid by curing it. Moreover, while the above embodiment is directed towards filling the vessel with a calibrant fluid, it should be understood that any appropriate fluid could be stored in the vessel, such as a wash fluid. Thus, the step of injecting a tonometered gas mixture is not always required.

An alternate method of manufacturing the device is illustrated in FIGS. 9-15. As illustrated in FIG. 9, the vessel 12 is initially open at both the end of the stem 14 as well as at the end of the large diameter portion 16. Referring to FIG. 10, with the vessel disposed such that the large diameter portion extends vertically upwardly, a polymer, in the form of a solid spherical ball 34, is inserted into the large diameter portion of the vessel. Thereafter, as illustrated in FIG. 11, the base 19 of the large diameter portion is sealed. After the base has been sealed, the position of the vessel is reversed such that the base is facing downwardly. With the vessel in this position, a tonometered gas mixture is injected into the vessel, as illustrated in FIG. 12, for the reason noted above. Thereafter, a needle 38 is inserted through the open end of the stem in such a manner as to maintain the position of the piston ball 34 at the base of the vessel as can be seen in FIG. 13. Referring to FIG. 14, the appropriate aqueous fluid 40 is then injected into the vessel up to the bottom of the stem. The ball expands, as shown in FIG. 14, so as to firmly contact the inner peripheral wall of the vessel to thereby provide an adequate piston seal. Finally, the open end of the stem is sealed as illustrated in FIG. 15.

FIGS. 16 and 17 illustrate the process by which the fluid is removed from the vessel manufactured using either of the methods described above. Referring to FIG. 16, the stem 14 of the vessel 12 is fractured at the ceramic band 20 by utilizing any appropriate means and the weakened area 21 of the base 19 of the vessel is fractured utilizing a push rod 42, or the like. Thereafter, the push rod is moved in the direction of arrows A, illustrated in FIG. 16, to thereby push the piston and correspondingly pump the fluid from the vessel.

Thus, according to the invention, the fluid can be pumped from the ampule with the ampule disposed in any orientation without effecting the position of the gases in the vessel, as discussed above. Moreover, the pump arrangement allows the fluid to be pumped from the ampule at a specific rate.

I claim:
1. A positive displacement ampule, comprising:
 a vessel for storing a fluid therein, said vessel having a breakable surface;
 piston means disposed in said vessel for forcing said fluid from said vessel;
 an opening in a wall of said vessel at a location spaced apart from said breakable surface and means for forming said opening; and
 means for fracturing said breakable surface for gaining access to the interior of said vessel through said breakable surface for then pushing said piston means in the direction of said opening, thereby pushing said fluid from said vessel through said opening.

2. The ampule of claim 1 wherein said piston means is a water-swellable polymer which expands when saturated with a fluid so as to function as a piston.

3. The ampule of claim 2 wherein said vessel is cylindrical in shape and wherein said polymer is initially smaller than an inside diameter of said vessel such that when said polymer is saturated with fluid, said polymer expands so as to press against the inside circumference of said vessel.

4. The ampule of claim 1 wherein said means for fracturing and pushing comprise a pin disposed external of said vessel for initially fracturing said breakable surface and pushing against said piston means.

5. The ampule of claim 4 wherein said breakable surface comprises a weakened portion in a surface of said vessel.

6. The ampule of claim 5 wherein said means for forming said opening comprises a weakened portion of one of a scored portion and a reduced thickness portion.

7. The ampule of claim 1 wherein one end of said vessel is a large diameter base portion and said other end is a small diameter stem portion, said base portion being joined to said stem portion.

8. The ampule of claim 7 wherein said stem portion has a weakened area circumscribing said other end for allowing said other end to be fractured to form said opening.

9. The ampule of claim 8 wherein said weakened portion is a ceramic band.

10. The ampule of claim 7 wherein the inside diameter of said stem portion is less than 1 mm.

11. A method of removing fluid from an ampule, said ampule being a vessel having a large diameter base portion at one end thereof joined to a small diameter stem portion at the other end thereof, a piston disposed in said vessel at the base end thereof and fluid disposed in said vessel between said piston and the stem end, said base end and said stem portion having first and second weakened areas, respectively, said method comprising the following steps:

fracturing said stem portion at said second weakened area;

puncturing said base end at said first weakened area using a push rod; and thereafter using said push rod to push said piston with said push rod extending through said base end so as to push said fluid from said vessel through said fractured stem portion.

* * * * *